United States Patent
Magna et al.

(10) Patent No.: US 10,150,108 B2
(45) Date of Patent: Dec. 11, 2018

(54) CATALYTIC COMPOSITION AND PROCESS FOR OLIGOMERIZING ETHYLENE INTO 1-HEXENE

(71) Applicant: IFP Energies nouvelles, Rueil-Malmaison (FR)

(72) Inventors: Lionel Magna, Lyons (FR); Sebastien Drochon, Grigny (FR); Helene Olivier-Bourbigou, Saint Genis-Laval (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/668,132

(22) Filed: Mar. 25, 2015

(65) Prior Publication Data

US 2015/0273456 A1    Oct. 1, 2015

(30) Foreign Application Priority Data

Mar. 25, 2014  (FR) ...................................... 14 52517

(51) Int. Cl.
| | |
|---|---|
| C07C 2/00 | (2006.01) |
| B01J 31/00 | (2006.01) |
| B01J 31/22 | (2006.01) |
| B01J 37/04 | (2006.01) |
| C07C 2/34 | (2006.01) |
| B01J 31/02 | (2006.01) |
| B01J 31/04 | (2006.01) |
| B01J 31/14 | (2006.01) |
| C07C 2/32 | (2006.01) |

(52) U.S. Cl.
CPC ....... *B01J 31/2208* (2013.01); *B01J 31/0204* (2013.01); *B01J 31/0214* (2013.01); *B01J 31/04* (2013.01); *B01J 31/143* (2013.01); *B01J 37/04* (2013.01); *C07C 2/32* (2013.01); *C07C 2/34* (2013.01); *B01J 2231/20* (2013.01); *B01J 2531/22* (2013.01); *B01J 2531/62* (2013.01); *C07C 2531/12* (2013.01); *C07C 2531/22* (2013.01); *C07C 2531/34* (2013.01); *Y02P 20/52* (2015.11)

(58) Field of Classification Search
CPC .... B01J 31/34; B01J 31/0204; B01J 31/0214; C07C 2/06; C07C 2/08
See application file for complete search history.

(56) References Cited

U.S. PATENT DOCUMENTS

| 5,731,487 A | 3/1998 | Tamura et al. | |
|---|---|---|---|
| 6,828,269 B2 * | 12/2004 | Commereuc | ........ B01J 31/0214 |
| | | | 502/113 |
| 6,844,290 B1 * | 1/2005 | Maas | ...................... B01J 31/143 |
| | | | 502/103 |
| 6,903,042 B2 * | 6/2005 | Drochon | .................. B01J 31/04 |
| | | | 502/150 |
| 2001/0023281 A1 | 9/2001 | Commereuc et al. | |

FOREIGN PATENT DOCUMENTS

| EP | 0614865 A1 | 9/1994 |
|---|---|---|
| FR | 2802833 A1 | 6/2001 |

OTHER PUBLICATIONS

Search Report dated Aug. 29, 2014 issued in corresponding FR 1452517 application (pp. 1-2).

\* cited by examiner

*Primary Examiner* — Rip A Lee
(74) *Attorney, Agent, or Firm* — Millen, White, Zelano & Branigan, PC

(57) ABSTRACT

A composition is described which comprises at least one chromium compound, at least one aryloxy compound of an element M selected from the group formed by magnesium, calcium, strontium and barium, with general formula $[M(RO)_{2-n}X_n]_y$, in which RO is an aryloxy radical of a derivative ROH containing 6 to 80 carbon atoms, X is a halogen or a hydrocarbyl radical containing 1 to 30 carbon atoms, n is a whole number which may take the values 0 or 1 and y is a whole number in the range 1 to 10, and at least one additive selected from ether type compounds, which may or may not be cyclic, introduced in a near-stoichiometric quantity with respect to the element M.

7 Claims, No Drawings

CATALYTIC COMPOSITION AND PROCESS FOR OLIGOMERIZING ETHYLENE INTO 1-HEXENE

The present invention relates to a novel composition comprising at least one chromium compound, at least one aryloxy compound of an element M and at least one additive selected from ether type compounds, and to a process for its preparation. The invention also relates to the use of said composition in a process for the trimerization of ethylene to 1-hexene.

In another aspect, the invention relates to an intermediate composition comprising at least one aryloxy compound of an element M and at least one additive selected from ether type compounds, and to a process for its preparation.

1-hexene plays a very important role as a reaction intermediate in the chemicals and petrochemicals industries. Its principal use is the production of various qualities of polyethylene, in which it is engaged as a co-monomer. This compound is currently principally obtained by oligomerizing ethylene. Current systems which are capable of selectively trimerizing ethylene into 1-hexene are essentially based on chromium (D. S. McGuinness, Chem. Rev. 2011, 111, 2321). Known systems for carrying out the selective production of 1-hexene which may be cited are the systems described, for example, in patents U.S. Pat. Nos. 5,198,563, 5,288,823, 5,382,738, EP-A-0 608 447, EP-A-0 611 743 and EP-A-0 614 865. These catalysts are prepared from a chromium salt and a metallic amide, in particular a pyrrolide. Other catalysts employ an aluminoxane and a chromium complex in association with phosphorus-containing ligands as described, for example, in patent U.S. Pat. No. 5,550,305.

Patent FR-B-2 802 833 in particular describes a catalytic composition obtained by mixing at least one chromium compound with at least one aryloxy compound of an element M selected from the group formed by magnesium, calcium, strontium and barium, with general formula $M(RO)_{2-n}X_n$, in which RO is an aryloxy radical containing 6 to 80 carbon atoms, X is a halogen or a hydrocarbyl radical containing 1 to 30 carbon atoms and n is a whole number which can take the values 0 to 2, and with at least one aluminium compound selected from the group formed by tris(hydrocarbyl)aluminium compounds and chlorine-containing or bromine-containing hydrocarbylaluminium compounds with general formula $AlR'_m Y_{3-m}$, in which R' is a hydrocarbyl radical containing 1 to 6 carbon atoms, Y is a chlorine or bromine atom and m is a number from 1 to 3, and aluminoxanes.

When carrying out a petrochemical process on an industrial scale in a continuous mode, the catalytic solution is injected at the same time as ethylene into a reactor which is stirred using conventional mechanical means or by external recirculation, and maintained at the desired temperature. It is also possible to inject the catalyst components separately into the reaction medium, such as, for example, the product of the interaction of the chromium compound with the aryloxy compound of the element M on the one hand and the hydrocarbyl aluminium compound on the other hand. In this case, the problem of the stability of the components employed arises, in particular that of the aryloxy compound of the element M or indeed that of the product of the interaction of the chromium compound with the aryloxy compound of the element M. Particular care has to be taken that these formulations do not become degraded (precipitation, gel formation, etc.) before or during their use in the process.

Surprisingly, it has now been discovered that a composition comprising at least one chromium compound, at least one aryloxy compound of an element M and at least one additive selected from ether type compounds introduced in a near-stoichiometric quantity with respect to the element M has an improved stability while retaining good activity and good selectivity when it is used in the ethylene trimerization reaction.

It has also been discovered that the intermediate composition comprising at least one aryloxy compound of an element M and at least one additive selected from ether type compounds introduced in a near-stoichiometric quantity with respect to the element M exhibits improved stability.

DETAILED DESCRIPTION OF THE INVENTION

The invention concerns a composition comprising:
  at least one chromium compound;
  at least one aryloxy compound of an element M selected from the group formed by magnesium, calcium, strontium and barium, preferably magnesium, with general formula $[M(RO)_{2-n}X_n]_y$, in which RO is an aryloxy radical of a derivative ROH containing 6 to 80 carbon atoms, X is a halogen or a hydrocarbyl radical containing 1 to 30 carbon atoms, n is a whole number which may take the values 0 or 1 and y is a whole number in the range 1 to 10, with y preferably being equal to 1, 2, 3 or 4;
  and at least one additive selected from ether type compounds, which may or may not be cyclic, introduced in a near-stoichiometric quantity with respect to the element M.

The invention also concerns an intermediate composition comprising:
  at least one aryloxy compound of an element M selected from the group formed by magnesium, calcium, strontium and barium, preferably magnesium, with general formula $[M(RO)_{2-n}X_n]_y$, in which RO is an aryloxy radical of a derivative ROH containing 6 to 80 carbon atoms, X is a halogen or a hydrocarbyl radical containing 1 to 30 carbon atoms, n is a whole number which may take the values 0 or 1 and y is a whole number in the range 1 to 10, with y preferably being equal to 1, 2, 3 or 4;
  and at least one additive selected from ether type compounds, which may or may not be cyclic, introduced in a near-stoichiometric quantity with respect to the element M.

Thus, in addition to the components of the intermediate composition, the composition of the invention comprises at least one chromium compound.

For reasons of clarity, the term "composition" in the remainder of the text shall mean the composition of the invention comprising at least one chromium compound, in contrast to the "intermediate composition" which does not comprise a chromium compound.

The invention also concerns the process for the preparation of said composition.

In a first embodiment, said process for the preparation of said composition comprises mixing:
  at least one chromium compound;
  at least one compound $MX_2$ of an element M selected from the group formed by magnesium, calcium, strontium and barium, X being a halogen or a hydrocarbyl radical containing 1 to 30 carbon atoms;

at least one derivative ROH in which RO is an aryloxy radical of a derivative ROH containing 6 to 80 carbon atoms;

and at least one additive selected from ether type compounds, which may or may not be cyclic, introduced in a near-stoichiometric quantity with respect to the element M.

In a second embodiment, the composition of the invention may also advantageously be prepared by adding at least one chromium compound to the intermediate composition as described above.

In the case in which the composition of the invention also comprises an aluminium compound, the process for the preparation of the composition of the invention may comprise, irrespective of whether it is for the first or the second embodiment described above, adding at least one aluminium compound selected from the group formed by tris(hydrocarbyl)aluminium compounds and chlorine- or bromine-containing hydrocarbylaluminium compounds with general formula $AlR'_m Y_{3-m}$, in which R' is a hydrocarbyl radical containing 1 to 6 carbon atoms, Y is a chlorine or bromine atom and m is a number from 1 to 3, and aluminoxanes, used alone or as a mixture.

The preparation process may optionally be carried out in the presence of a solvent.

The invention also concerns a process for the preparation of said intermediate composition, comprising mixing:

at least one compound $MX_2$ of an element M selected from the group formed by magnesium, calcium, strontium and barium, X being a halogen or a hydrocarbyl radical containing 1 to 30 carbon atoms;

at least one derivative ROH in which RO is an aryloxy radical of a derivative ROH containing 6 to 80 carbon atoms;

and at least one additive selected from ether type compounds, which may or may not be cyclic, introduced in a near-stoichiometric quantity with respect to the element M.

The order of mixing the compound $MX_2$, the derivative ROH and the additive is not critical; mixing can optionally be carried out in a solvent.

Without wishing to be bound by any particular theory, the Applicant considers that the interaction of a compound $MX_2$ of an element M defined in accordance with the invention and at least one derivative ROH as defined in the invention results in the formation of at least one polymeric compound with general formula $[M(RO)_{2-n}X_n]_y$, in which M is selected from the group formed by magnesium, calcium, strontium and barium, RO is an aryloxy radical of a derivative ROH containing 6 to 80 carbon atoms, X is a halogen or a hydrocarbyl radical containing 1 to 30 carbon atoms, n is a whole number which may take the values 0 or 1 and y is a whole number in the range 1 to 10.

The chromium compound present in the composition of the invention may comprise one or more identical or different anions selected from the group formed by halides, carboxylates, acetylacetonates, and alkoxy and aryloxy anions. The chromium compound may be a chromium(III) or chromium(III) salt, but may also be a salt with a different oxidation number and may include one or more identical or different anions such as, for example, halides, carboxylates, acetylacetonates, alkoxy anions or aryloxy anions. The chromium compounds which are preferably used in the invention are chromium(III) compounds as they are more accessible, but a chromium(I) or chromium(II) compound may also be suitable.

In the composition of the invention and the intermediate composition of the invention, X is advantageously a halogen (chlorine or bromine) or a hydrocarbyl radical containing 1 to 30 carbon atoms, which may be linear or branched, for example alkyl, aryl, or aralkyl, aryl or substituted cycloalkyl, preferably a hydrocarbyl residue containing 2 to 10 carbon atoms.

In the composition of the invention and the intermediate composition of the invention, the aryloxy radical RO of the alcohol derivative ROH preferably has the general formula:

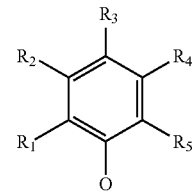

in which $R_1$, $R_2$, $R_3$, $R_4$ and $R_5$, which may be identical or different, each represent a hydrogen atom, a halogen atom or a hydrocarbyl radical, for example alkyl, cycloalkyl, alkenyl, aryl or aralkyl, aryl or substituted cycloalkyl, preferably containing 1 to 16 carbon atoms, and more particularly 1 to 10 carbon atoms. By way of a non-limiting list of examples, $R_1$, $R_2$, $R_3$, $R_4$ and $R_5$ may be a methyl, ethyl, n-propyl, isopropyl, n-butyl, tert-butyl, cyclohexyl, benzyl, phenyl, 2-methylphenyl, 2,6-dimethylphenyl, 2,4,6-trimethylphenyl or 2-methyl-2-phenylprop-1-yl radical.

Non-limiting examples of preferred aryloxy radicals which may be cited are: 4-phenylphenoxy, 2-phenylphenoxy, 2,6-diphenylphenoxy, 2,4,6-triphenylphenoxy, 2,3,5,6-tetraphenylphenoxy, 2-tert-butyl-6-phenylphenoxy, 2,4-ditert-butyl-6-phenylphenoxy, 2,6-diisopropylphenoxy, 2,6-dimethylphenoxy, 2,6-ditert-butylphenoxy, 4-methyl-2,6-ditert-butylphenoxy, 2,6-dichloro-4-tert-butylphenoxy and 2,6-dibromo-4-tert-butylphenoxy. The two aryloxy radicals may be carried by the same molecule such as, for example, the biphenoxy, binaphthoxy or 1,8-naphthalene-dioxy radical, which may or may not be substituted with alkyl, aryl or halide radicals. Preferably, the aryloxy radical RO is 2,6-diphenylphenoxy, 2-tert-butyl-6-phenylphenoxy or 2,4-ditert-butyl-6-phenylphenoxy.

The additive as described in the composition of the invention and the intermediate composition of the invention is selected from ether type compounds, which may or may not be cyclic. It is preferably selected from diethyl ether, dibutyl ether, diisopropylether, 2-methoxy-2-methylpropane, 2-methoxy-2-methylbutane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl)ether and benzofuran, used alone or as a mixture. Preferably, the additive is dibutyl ether.

In one embodiment, the composition of the invention comprising the chromium compound may also comprise at least one aluminium compound (also termed a co-catalyst) selected from the group formed by tris(hydrocarbyl)aluminium and chlorine- or bromine-containing hydrocarbylaluminium compounds with general formula $AlR'_m Y_{3-m}$, in which R' is a hydrocarbyl radical containing 1 to 6 carbon atoms, Y is a chlorine or bromine atom and m is a number from 1 to 3, and aluminoxanes, used alone or as a mixture. When at least one chromium compound is present in the composition, the molar ratio between the aluminium compound and the chromium compound (Al/Cr) is advantageously in the range 1:1 to 35:1.

The aluminium compounds used as a co-catalyst are selected from hydrocarbylaluminium-tris(hydrocarbyl)aluminium compounds, chlorine-containing or bromine-containing hydrocarbylaluminium compounds and aluminoxanes. The tris(hydrocarbyl)aluminium compounds and the chlorine- or bromine-containing hydrocarbylaluminium compounds are represented by the general formula $AlR'_m Y_{3-m}$, in which R' is a hydrocarbyl radical containing 1 to 6 carbon atoms, Y is a chlorine or bromine atom, preferably a chlorine atom, and m is a number from 1 to 3. Non-limiting examples which may be cited are: dichloroethylaluminium, ethylaluminium sesquichloride, chlorodiethylaluminium, chlorodiisobutylaluminium, triethylaluminium, tripropylaluminium, triisobutylaluminium, methylaluminoxane. The preferred hydrocarbyl aluminium compound is triethylaluminium.

The composition of the invention and the intermediate composition of the invention may be in solution in a solvent constituted by a saturated hydrocarbon such as hexane, cyclohexane, heptane, butane, isobutane, by an unsaturated hydrocarbon such as a monoolefin or a diolefin containing 4 to 20 carbon atoms, for example, or by an aromatic hydrocarbon such as benzene, toluene, ortho-xylene, mesitylene or ethylbenzene, pure or as a mixture. The concentration of chromium in the solution may be from $1 \times 10^{-8}$ to 2 mole/L, preferably $1 \times 10^{-7}$ to 1 mole/L.

The compositions of the invention comprising chromium have a molar ratio between the element M and the chromium (ratio M/Cr) which is advantageously in the range 1:1 to 30:1, preferably in the range 1:1 to 20:1.

In accordance with the invention, the term "near-stoichiometric quantity with respect to the element M" means a molar ratio between the ether type additive and the element M (ether/M ratio) which may be in the range 1 to 200, preferably in the range 1 to 100 and still more preferably in the range 1 to 60, or even in the range 1 to 40.

In a further aspect, the invention concerns a process for the trimerization of ethylene using the composition of the invention.

When carrying out a trimerization process, the various constituents of the composition of the invention, namely the chromium compound, the aryloxy compound of the element M and the additive as described in the invention, as well as any co-catalyst, may be injected into the reactor simultaneously or in a sequential manner, separately or as a mixture. The ethylene trimerization process of the invention may be carried out in continuous or discontinuous mode.

In a particular embodiment, the ethylene trimerization process of the invention is carried out discontinuously in accordance with the following steps:

in a reactor under an atmosphere of ethylene, introducing the composition of the invention comprising at least one chromium compound, at least one aryloxy compound of an element M selected from the group formed by magnesium, calcium, strontium and barium, with general formula $[M(RO)_{2-n}X_n]_y$, in which RO is an aryloxy radical of a derivative ROH containing 6 to 80 carbon atoms, X is a halogen or a hydrocarbyl radical containing 1 to 30 carbon atoms, n is a whole number which may take the values 0 or 1 and y is a whole number in the range 1 to 10, and at least one additive selected from ether type compounds which may or may not be cyclic, introduced in a near-stoichiometric quantity with respect to the element M;

introducing ethylene at the desired pressure;
adjusting the temperature to the desired value;
and adding the aluminium compound defined above.

The reactor used is advantageously provided with the usual stirring, heating and cooling devices. Advantageously, the reactor is initially purged by means of vacuum/argon cycles.

The trimerization reactor is advantageously maintained at constant pressure by introducing ethylene until the total volume of liquid produced represents, for example, 2 to 50 times the volume of the catalytic solution introduced at the beginning. Next, the catalyst is destroyed by any of the usual means known to the skilled person, then the reaction products and the solvent are withdrawn and separated.

In another particular embodiment, the ethylene trimerization process of the invention is carried out continuously by simultaneous and separate injection:

of the constituents of the composition, i.e.:
  at least one chromium compound;
  at least one aryloxy compound of an element M selected from the group formed by magnesium, calcium, strontium and barium, with general formula $[M(RO)_{2-n}X_n]_y$, in which RO is an aryloxy radical of a derivative ROH containing 6 to 80 carbon atoms, X is a halogen or a hydrocarbyl radical containing 1 to 30 carbon atoms, n is a whole number which may take the values 0 or 1, and y is a whole number in the range 1 to 10;
at least one additive selected from ether type compounds, which may or may not be cyclic, introduced in a near-stoichiometric quantity with respect to the element M;
at least one aluminium compound as described above;
and ethylene;
into a reactor, the whole system being maintained at the desired temperature and pressure.

The reactor used is advantageously stirred by conventional mechanical means or by external recirculation.

The ethylene is advantageously introduced into the reactor via a pressure-controlled intake valve which keeps the pressure constant. The reaction mixture is withdrawn by means of a liquid level-controlled valve so as to keep the liquid level constant. The catalyst is continuously destroyed by any of the usual means known to the skilled person, then the reaction products as well as the solvent are separated, for example by distillation. The ethylene which has not been transformed may be recycled to the reactor.

The ethylene trimerization reaction may be carried out at a total pressure of 0.5 to 15 MPa, preferably 1 to 8 MPa, and at a temperature of 20° C. to 180° C., preferably 50° C. to 160° C.

The following examples illustrate the invention without limiting its scope.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 14/52.517, filed Mar. 25, 2014 is incorporated by reference herein.

EXAMPLES

In the examples below, the term "OPh" denotes the radical 2-tert-butyl-6-phenyl phenoxy. The acronym "DBE" shall be used for dibutylether. The formula "$Cr(2-EH)_3$" shall be used to describe chromium tris(2-ethylhexanoate).

Example 1

(Not in Accordance with the Invention): Synthesis of a 0.3 mol/L Solution of $Mg(OPh)_2$ in a Cyclohexane/Heptane Mixture (Solution A)

12.2 g of 2-tert-butyl-6 phenyl phenol (54 mmol) diluted in 47 mL of cyclohexane was introduced into a 200 mL Schlenk flask under argon. Next, 22.5 g (27 mmol, 30.9 mL) of a 20% by weight solution of butyl-octylmagnesium in n-heptane was added. This solution was stirred under argon for approximately 1 h. The solution obtained was initially homogeneous and colourless. After only 12 h at 3° C., the formation of a white precipitate was observed which confirmed the absence of physical stability for this formulation.

Example 2

(In Accordance with the Invention): Synthesis of the Intermediate Composition "$Mg(OPh)_2/DBE$" (1/5 mol/mol), 0.3 mol/L, in a Cyclohexane/Heptane Mixture (Solution B)

This solution was prepared using the protocol described in Example 1. 12.2 g of 2-tert-butyl-6-phenyl phenol (54 mmol), 17.6 g of dibutyl ether (135 mmol, 23 mL), 24 mL of cyclohexane and 22.5 g (27 mmol, 30.9 mL) of a 20% by weight solution of butyl-octylmagnesium in n-heptane were brought together and a homogeneous, colourless solution was obtained which remained stable for more than 12 months at ambient temperature as well as at 3° C.

Example 3

(In Accordance with the Invention): Synthesis of the Intermediate Composition "$Mg(OPh)_2/DBE$" (1/10 mol/mol), 0.3 mol/L, in a Cyclohexane/Heptane Mixture (Solution C)

This solution was prepared using the protocol described in Example 1. 12.2 g of 2-tert-butyl-6-phenyl phenol (54 mmol), 35.1 g of dibutyl ether (270 mmol, 46 mL) and 22.5 g (27 mmol, 30.9 mL) of a 20% by weight solution of butyl-octylmagnesium in n-heptane were brought together, and a homogeneous, colourless solution was obtained which remained stable for more than 12 months at ambient temperature as well as at 3° C.

Example 4

(Accordance with the Invention): Synthesis of the Intermediate Composition "$Mg(OPh)_2/DBE$" (1/39 mol/mol), 0.12 mol/L, in a Cyclohexane/Heptane Mixture (Solution D)

This solution was prepared using the protocol described in Example 1. 4.7 g of 2-tert-butyl-6-phenyl phenol (20.7 mmol), 52.9 g of dibutyl ether (406 mmol, 69.2 mL) and 8.6 g (10.4 mmol, 11.8 mL) of a 20% by weight solution of butyl-octylmagnesium in n-heptane were brought together; a homogeneous, colourless solution was obtained which remained stable for more than 12 months at ambient temperature as well as at 3° C.

Example 5

(Not in Accordance with the Invention): Synthesis of a 0.3 mol/L Solution of "$Cr(2-EH)_3/Mg(OPh)_2$" in a Cyclohexane/Heptane Mixture (Solution E)

13.6 g of 2-tert-butyl-6 phenyl phenol (60 mmol) which had been diluted in 33 mL of cyclohexane was introduced into a 200 mL Schlenk flask under argon. Next, 25 g (30 mmol, 34.3 mL) of a 20% by weight solution of butyl-octylmagnesium in n-heptane was added. The solution was stirred under argon at ambient temperature for 1 h. 19.5 g of $Cr(2-EH)_3$ containing 8% by weight of chromium (30 mmol, 19.3 mL) was introduced into a second 200 mL Schlenk flask under argon. The pre-prepared solution of $Mg(OPh)_2$ was added to this compound. After stirring for 2 h at ambient temperature, this solution was homogeneous and green in colour. However, after 12 h at ambient temperature, the formation of a gel was observed which was deposited at the bottom of the Schlenk preparation flask, which confirmed the absence of physical stability for this formulation.

Example 6

(In Accordance with the Invention): Synthesis of the Composition "$Cr(2-EH)_3/Mg(OPh)_2/DBE$" (1/1/5 mol/mol/mol), 0.3 mol/L, in a Cyclohexane/Heptane Mixture (Solution F)

12.2 g of 2-tert-butyl-6 phenyl phenol (54 mmol), 17.6 g of dibutyl ether (135 mmol, 23 mL) as well as 6.5 mL of cyclohexane were introduced into a 200 mL Schlenk flask under argon. Next, 22.5 g (27 mmol, 30.9 mL) of a 20% by weight solution of butyl-octylmagnesium in n-heptane was introduced. The solution was stirred under argon at ambient temperature for 1 h. 17.5 g of a solution of $Cr(2-EH)_3$ containing 8% by weight of chromium (i.e. 27 mmol, 17.4 mL) was introduced into a second 200 mL Schlenk flask under argon. The pre-prepared solution of $Mg(OPh)_2$ was added to this compound. A homogeneous green-coloured solution was thus obtained which remained stable for more than 12 months at ambient temperature as well as at 3° C.

Examples 7 to 9

Evaluation of Catalytic Performances of Solution F

The ethylene trimerization tests presented in the table below were carried out in a stainless steel autoclave with a useful volume of 250 mL provided with a jacket to allow the temperature to be regulated by circulating oil. 43 mL of cyclohexane as well as 3.4 mL of a 0.03 mol/L chromium solution prepared directly from the composition F (Solution F) and cyclohexane were introduced under an ethylene atmosphere and at ambient temperature. Once the temperature of the reactor had been raised to 140° C., 2.5 equivalent (with respect to the chromium) of triethylaluminium (pre-diluted in cyclohexane) was introduced under ethylene pressure. The ethylene pressure was maintained at 3 MPa. After 1 h of reaction, ethylene introduction was halted and the reactor was cooled and degas sed, then the gas and the liquid which had been withdrawn using a syringe were analysed by gas phase chromatography. The composition of the products obtained is given in the table below:

| Ex. | Cr/Mg(OPh)$_2$/DBE molar ratio | Maturation | Activity (g/gCr/h) | Sel. C4 (% by wt) | Sel. C6 (% by wt) | Sel. C8 (% by wt) | Sel. C10 (% by wt) | Sel. Waxes (% by wt) |
|---|---|---|---|---|---|---|---|---|
| 7 | 1/1/5 | Sol. F freshly prepared | 6000 | 1 | 72 | 1 | 10 | 15 |
| 8 | 1/1/5 | Sol. F matured 4 months | 6200 | 1 | 74 | 1 | 9 | 14 |
| 9 | 1/1/5 | Sol. F matured 14 months | 6400 | 1 | 72 | 1 | 9 | 15 |

(Sol. = solution, Sel. = selectivity; wt = weight)

These examples demonstrate the chemical stability of the formulations as described in the invention.

Examples 10 to 11

Evaluation of Catalytic Performances of Compositions Starting from an Intermediate Composition B The ethylene trimerization tests presented in the table below were carried out in a stainless steel autoclave with a useful volume of 250 mL, provided with a jacket to allow the temperature to be regulated by circulating oil. 43 mL of cyclohexane as well as 3.4 mL of a 0.03 mol/L chromium solution prepared directly from the intermediate composition B (Solution B), an 8% by weight of Cr solution of Cr(-EH)$_3$ and cyclohexane were introduced under an ethylene atmosphere and at ambient temperature. Once the temperature of the reactor had been raised to 140° C., 2.5 equivalent (with respect to the chromium) of triethylaluminium (pre-diluted in cyclohexane) was introduced under ethylene pressure. The ethylene pressure was maintained at 3 MPa. After 1 h of reaction, ethylene introduction was halted and the reactor was cooled and degassed, then the gas and the liquid which had been withdrawn using a syringe were analysed by gas phase chromatography. The composition of the products obtained is given in the table below:

| Ex. | Molar ratio Cr/Mg(OPh)$_2$/DBE | Maturation | Activity (g/gCr/h) | Sel. C4 (% by wt) | Sel. C6 (% by wt) | Sel. C8 (% by wt) | Sel. C10 (% by wt) | Sel. Waxes (% by wt) |
|---|---|---|---|---|---|---|---|---|
| 10 | 1/1/5 | Sol. B freshly prepared | 5100 | 1 | 74 | 0 | 10 | 13 |
| 11 | 1/1/5 | Sol. B matured 16 months | 8000 | 1 | 69 | 1 | 12 | 16 |

(Sol. = solution, Sel. = selectivity; wt = weight)

These examples demonstrate the chemical stability of the formulations as described in the invention.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A process for the preparation of a kit comprising
   a) at least one chromium compound and
   b) an intermediate composition comprising:
      at least one aryloxy compound of an element M selected from the group consisting of magnesium, calcium, strontium and barium, with general formula [M(RO)$_{2-n}$X$_n$]$_y$, in which RO is an aryloxy radical of a derivative ROH containing 6 to 80 carbon atoms, X is a halogen or a hydrocarbyl radical containing 1 to 30 carbon atoms, n is a whole number which may take the integer values 0 or 1 and y is a whole number in the range 1 to 10;
      at least one additive selected from ether compounds, wherein the additive is diethyl ether, dibutyl ether, diisopropylether, 2-methoxy-2-methylpropane, 2-methoxy-2-methylbutane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether or benzofuran, or a mixture thereof, and wherein the molar ratio between the additive and the element M is in the range of 1 to 60, comprising;
   a) mixing:
      at least one compound MX$_2$ of an element M selected from the group consisting of magnesium, calcium, strontium and barium, X being a halogen or a hydrocarbyl radical containing 1 to 30 carbon atoms;
      at least one derivative ROH in which RO is an aryloxy radical of a derivative ROH containing 6 to 80 carbon atoms;
      and at least one additive selected from ether compounds, which may or may not be cyclic, introduced in a near-stoichiometric quantity with respect to the element M to form an intermediate composition, and
   b) pairing said intermediate composition with at least one chromium compound.
2. A process for preparing a composition comprising mixing:
   at least one chromium compound;
   at least one compound MX$_2$ of an element M selected from the group consisting of magnesium, calcium, strontium and barium, X being a halogen or a hydrocarbyl radical containing 1 to 30 carbon atoms;
   at least one derivative ROH in which RO is an aryloxy radical of a derivative ROH containing 6 to 80 carbon atoms; and at least one additive selected from ether compounds, which may or may not be cyclic, introduced in a near-stoichiometric quantity with respect to the element M;

optionally, at least one aluminium compound selected from the group consisting of tris(hydrocarbyl)aluminium compounds, chlorine- or bromine-containing hydrocarbylaluminium compounds with general formula $AlR'_m Y_{3-m}$, in which R' is a hydrocarbyl radical containing 1 to 6 carbon atoms, Y is a chlorine or bromine atom and m is a number from 1 to 3, and aluminoxanes, used alone or as a mixture;

optionally, at least one solvent.

3. The process of claim 2 further comprising contacting the composition with a feed of ethylene to be transformed by an ethylene trimerization reaction.

4. An ethylene trimerization process carried out discontinuously in accordance with the following steps:

introducing at least one chromium compound;

at least one compound $MX_2$ of an element M selected from the group consisting of magnesium, calcium, strontium and barium, X being a halogen or a hydrocarbyl radical containing 1 to 30 carbon atoms;

at least one derivative ROH in which RO is an aryloxy radical of a derivative ROH containing 6 to 80 carbon atoms; and at least one additive selected from ether compounds, which may or may not be cyclic, introduced in a near-stoichiometric quantity with respect to the element M into a reactor;

introducing ethylene at a desired pressure;

adjusting the temperature to a desired value;

and adding at least one aluminium compound selected from the group consisting of tris(hydrocarbyl)aluminium compounds, chlorine- or bromine-containing hydrocarbylaluminium compounds with general formula $AlR'_m Y_{3-m}$, in which R' is a hydrocarbyl radical containing 1 to 6 carbon atoms, Y is a chlorine or bromine atom and m is a number from 1 to 3, and aluminoxanes, used alone or as a mixture.

5. An ethylene trimerization process carried out continuously by simultaneously and separately injecting at least one chromium compound;

at least one compound $MX_2$ of an element M selected from the group consisting of magnesium, calcium, strontium and barium, X being a halogen or a hydrocarbyl radical containing 1 to 30 carbon atoms;

at least one derivative ROH in which RO is an aryloxy radical of a derivative ROH containing 6 to 80 carbon atoms;

at least one additive selected from ether compounds, which may or may not be cyclic, introduced in a near-stoichiometric quantity with respect to the element M;

at least one aluminium compound selected from the group consisting of tris(hydrocarbyl)aluminium, chlorine- or bromine-containing hydrocarbylaluminium compounds having general formula $AlR'_m Y_{3-m}$ in which R' is a hydrocarbyl radical containing 1 to 6 carbon atoms, Y is a chlorine or bromine atom and m is a number from 1 to 3, and aluminoxanes, used alone or as a mixture; and ethylene into a reactor, the whole system being maintained at a desired temperature and pressure.

6. The process according to claim 4, in which the ethylene trimerization reaction is carried out at a total pressure of 0.5 to 15 MPa and at a temperature of 20° C. to 180° C.

7. The process of claim 2, wherein the at least one additive is suitable as a complexing agent for chromium.

* * * * *